United States Patent [19]

Orimoto et al.

[11] Patent Number: 5,131,830
[45] Date of Patent: * Jul. 21, 1992

[54] MULTI-LAYER MOLDING NOZZLE

[75] Inventors: Hiroyuki Orimoto; Katsumasa Yokota; Hidehiko Fukai; Koichi Sato, all of Sakakimachi, Japan

[73] Assignee: Nissei ASB Machine Co., Ltd., Japan

[*] Notice: The portion of the term of this patent subsequent to Jul. 9, 2008 has been disclaimed.

[21] Appl. No.: 643,444

[22] Filed: Jan. 18, 1991

Related U.S. Application Data

[63] Continuation of Ser. No. 381,650, Jun. 30, 1989, Pat. No. 5,030,077.

[51] Int. Cl.5 .............................................. B29C 45/22
[52] U.S. Cl. ..................................................... 425/130
[58] Field of Search ................... 425/130, 131.1, 133.1, 425/562, 563, 564, 565, 566, 568, 132, 133.5, 573; 264/328.8, 328.13; 137/114

[56] References Cited

U.S. PATENT DOCUMENTS

| | | | |
|---|---|---|---|
| 3,976,226 | 8/1976 | Monnet | 425/130 |
| 4,659,531 | 4/1987 | Ezaki | 425/112 |
| 4,808,101 | 2/1989 | Schad et al. | 425/130 |
| 5,030,077 | 7/1991 | Orimoto et al. | 425/562 |

Primary Examiner—Tim Heitbrink
Attorney, Agent, or Firm—Ostrolenk, Faber, Gerb & Soffen

[57] ABSTRACT

A multi-layer forming nozzle includes a valve member which can open and close a flow passage for molten resin which forms an intermediate layer of a multi-layer molded product by injection molding. The valve member is operated in response to resin pressure differentials at the front and back of the valve member to accurately switch from a multi-layer operation to a single layer operation and vice versa. A three-layer nozzle in accordance with the invention has a nozzle body provided interiorly with a first resin path, a second resin path and a third resin path in the form of a concentric circle bending to the same injection opening. The valve member is located either in a mouth portion of the third resin path in the central portion positioned internally of a mouth portion of the second resin path or a mouth portion of the second resin path in the intermediate portion positioned internally of the first resin path. The valve member is moved forward and backward in response to resin pressure differentials to open and close the valve member.

21 Claims, 4 Drawing Sheets

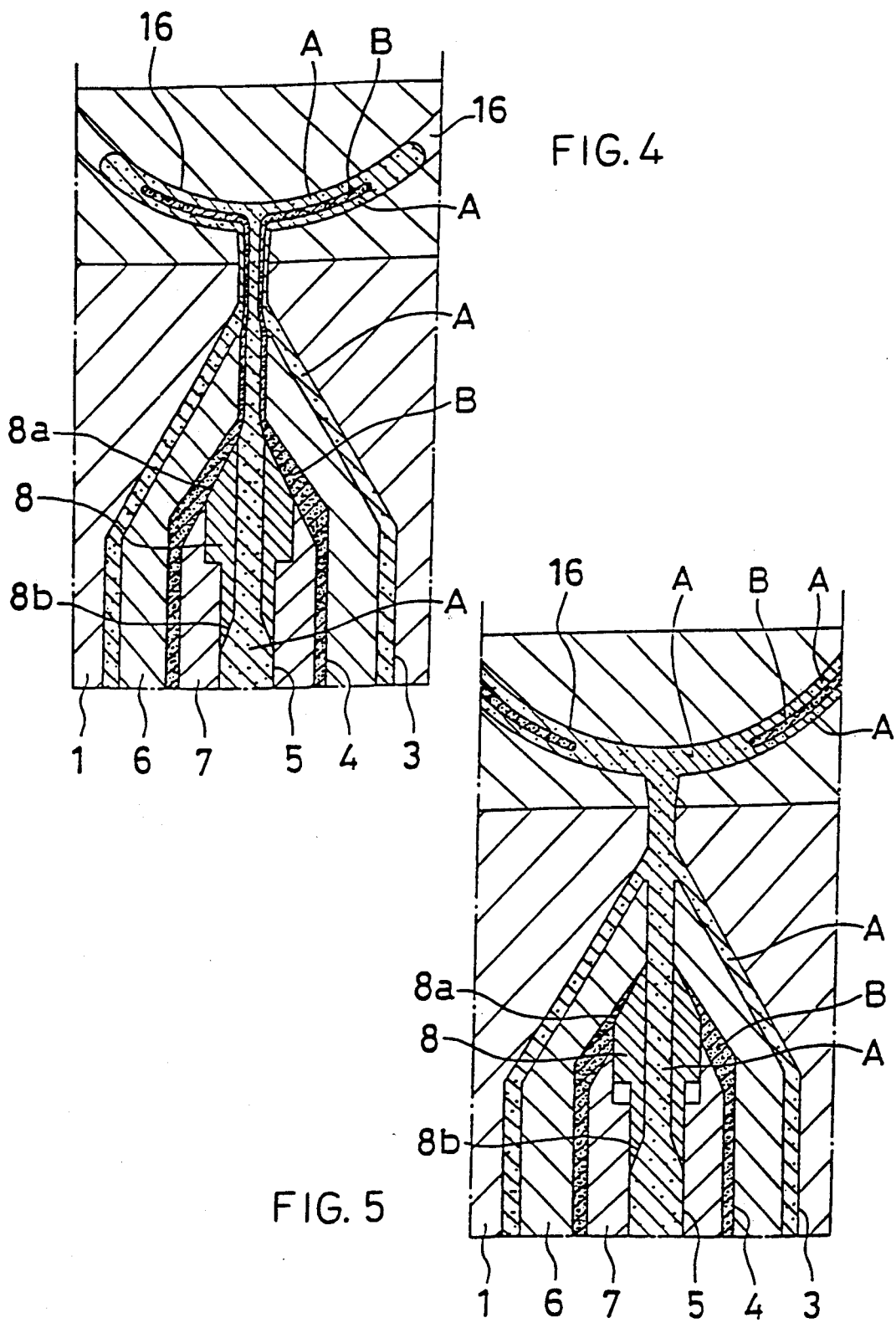

MULTI-LAYER MOLDING NOZZLE

The present application is a continuation of application Ser. No. 07/381,650, filed Jun. 30, 1989 now U.S. Pat. No. 5,030,077.

FIELD OF THE ART

This invention relates to a multi-layer molding nozzle used when a synthetic resin molded product whose sectional construction is multilayered is injection molded.

BACKGROUND

A conventional multi-layer molding nozzle comprises a multiple nozzle in which a nozzle body having a central mouth portion at a tip thereof is provided interiorly with a plurality of concentric resin paths, and different molten resins in the respective resin paths can be cavity-injected from said mouth of the nozzle The formation of a synthetic resin molded product into a multi-layer causes the quality of a thin-wall molded product (such as a beverage container) to be further improved by the resin present as an intermediate layer However, this poses a problem in that because of the provision of the intermediate layer, the shock resistance of the product is lowered or the cost of the product is lowered or the cost of the product increases, as compared with single layer products.

In view of the foregoing, an attempt has been made to use a conventional double or three-layer nozzle to control injection pressure, time, injection timing or the like of the molten resin which forms an intermediate layer so as to injection-mold a product partly having an intermediate layer. However, it has been very difficult to mold an intermediate layer within a predetermined range in terms of resin pressure.

Alternatively, a multiple nozzle is used in which a central path of a multiple resin path is made movable so that orifices of resin paths are selectively opened and closed to control molten resin, as disclosed in Japanese Patent Application Laid-Open No. 60-34819. However, in this case, a special valve device is required to control a flow of molten resin entering the central path passing through the orifice for injection, and in addition, the valve device is mechanically operated, and the nozzle has an extremely complicated construction.

DISCLOSURE OF THE INVENTION

This invention has been achieved in order to solve the above-described problems with respect to the conventional multiple nozzle. An object of this invention is to provide a new multi-layer molding nozzle which is simple in construction, and in which a flowpassage of molten resin which is to form an intermediate layer is opened and closed by a valve member to be operated by resin pressure to always accurately switch a multiple layer to a single layer and vice versa.

This invention having the aforesaid object overcomes the aforementioned problem encountered in the prior art by a three-layer nozzle in which a nozzle body is interiorly provided with a first resin path, a second resin path and a third resin path having the same injection opening in a concentric fashion, in which multiple nozzle, a mouth portion of the central third resin path located internally of a mouth portion of the second resin path is constituted by a valve member which is moved forward and backward by resin pressure of the third resin path and the second resin path to open and close the second resin path, and a mouth portion of the intermediate second resin path located internally of the first resin path is constituted by a valve member which is moved forward and backward by resin pressure of the second resin path and the first resin path to open and close the second resin path.

In the above-described structure, the molten resins of the respective resin paths applied with injection pressure are simultaneously injected from the mouth portion of the respective resin paths to cavities through the mouth portion of the nozzle. When the injection pressure of the second resin path is removed during the injection, the valve member is moved forward or backward by the resin pressure of the first or third resin path to close the second resin path to stop an outflow of the molten resin from the second resin path. Because of this, the molten resins of the first and third resin paths are merely injected to the cavity.

When injection pressure is applied to the second resin path, the valve member is moved backward or forward due to a difference in pressure receiving area in the valve member to open the second resin path, and the molten resin is injected to the cavity together with the molten resin of the other resin paths.

Accordingly, when the same kind of molten resin is used for the first and third resin paths and the different kind of molten resin is used for the second resin path, a molded product produced thereat is composed of a 2-kind 3-layer portion and a single layer portion.

This invention will be further described in detail by way of examples shown in the drawings

BRIEF DESCRIPTION OF THE DRAWINGS

The drawings show embodiments of a multilayer molding nozzle according to this invention in which:

FIGS. 4 and 5 are respectively sectional views showing the molding steps; and

BEST MODE FOR CARRYING OUT THE INVENTION

Figure 1:
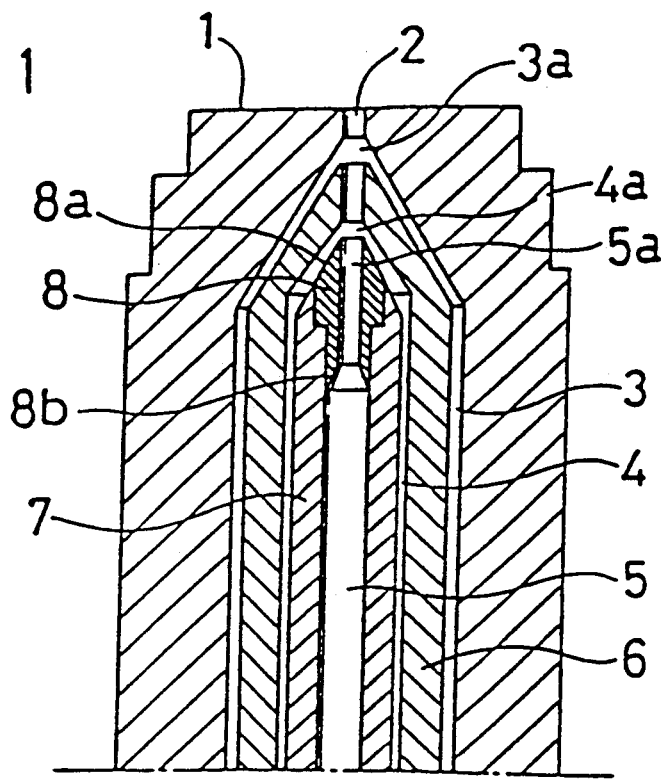
FIG. 1 is a sectional view of a first embodiment.

A nozzle body 1 is provided with an injection opening 2 formed centrally in the end surface of nozzle body 1. A first resin path 3, a second resin path 4 and a third resin path 5 are provided in the interior of the body 1 in a concentric fashion.

The three resin paths are defined by the cooperation between the first hollow core member 6, the second hollow core member 7 having a spacer on the side thereof and the interior of the body 1. The core members 6 and 7 are inserted in order through an opening at the rear end of the nozzle body 1.

The three-layer nozzle shown in FIG. 1 has a construction in which a mouth portion 3a of the first resin path 3 connected to the injection opening 2 is internally provided with a mouth portion 4a of the resin path 4, and a mouth portion 4a of the second resin path 4 is internally provided with a mouth portion 5a of the third resin path 5, the mouth portion 5a being formed from a valve member 8.

The valve member 8 comprises an annular body which is inserted so as to appear in the inner side of the end of the second core member 7. The inside diameter of the valve member 8 is substantially equal to the inside diameter of the mouth portion of the first resin path 3 and is smaller than the diameter of the third resin path 5, and the fore end 8a and the rear end 8b thereof are formed into a tapered surface on which resin pressure is exerted.

The ratio of a pressure receiving area of the ends 8a located in the second resin path 4 to the pressure receiving area of the end 8b located in the third resin path 5 is preferably greater than 0.5 and less than 4 in the projection plane. As long as the aforementioned ratio is satisfied, the valve member 8 will be moved downwardly into the end of the second core member 7 to maintain the second resin path 4 open even if the resin pressure of the third resin path 5 is somewhat greater than the resin pressure in the second resin path 4 during the injection operation. When the injection pressure of the second resin path 4 is made remarkably lower than (sufficiently low to overcome the ratio of the surface areas) the resin pressure of the third resin path 5, the valve member 8 will immediately move forward due to the resin pressure of third resin path 5 exerting on the rear end 8b to close the second resin path 4.

Accordingly, the valve member 8 is operated to open and close the second resin path 4 according to a difference between the resin pressures exerted on the opposite ends of the valve 8 to control the injection of the molten resin from the second resin path 4.

Figure 2:
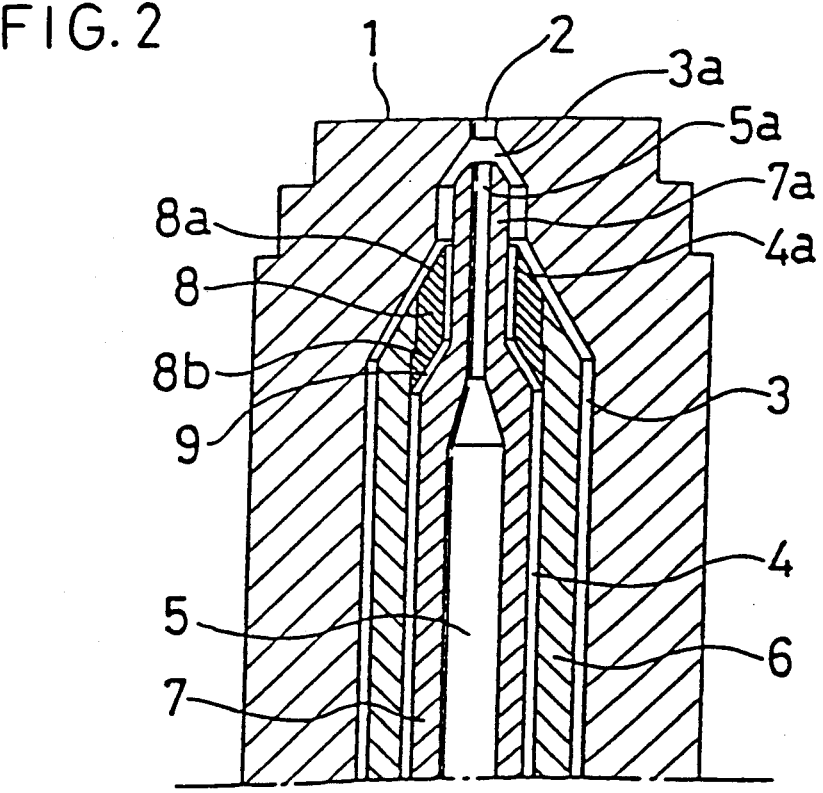
FIG. 2 is a sectional view of a second embodiment thereof.

A second embodiment of a three-layer nozzle in accordance with the present invention is shown in FIG. 2. In this embodiment the opening and closing of the second resin path 4 may be accomplished by the resin pressure of the first resin path 3, and the valve member is inserted in the end of the first core member 6.

In this case, since the second resin path 4 is closed by the backward movement of the valve member 8, the end 7a of the second core member 7 is reduced in diameter and extends to the front of the first resin path 3, the mouth portion 5a of the third resin path is made to extend to the inner side of the mouth portion 3a, the second resin path 4 is opened at the side of the end 7a of the second core member 7, and the mouth portion 4a is constituted by the valve member 8 located at the periphery of the end 7a of the second core member 7 inserted into the end of the first core member 6. The inside diameter of the valve member 8 is larger than the outside diameter of the end portion 7a of the second core member 7 to form a portion of the second resin path 4 between it and the second core member 7, and when the rear end 8b comes into contact with a tapered shoulder 9 formed in the outer surface of the second core member 7, the second resin path 4 is closed.

The ratio of a pressure receiving area of the fore end 8a to the pressure receiving area of the rear end 8b of the valve member 8 is preferably greater than 0.5 but less than 4 in the projection plane The resins supplied to the respective resin paths are suitably selected depending on the products to be molded, and in case of 3-kinds of resins and 5-layers, different resins are supplied to the respective resin paths. In the case where a product having 2-kinds of resins and 3-layers is injection molded, the resin material of the first resin path 3 is the same as that of the third resin path 5.

Figure 3:
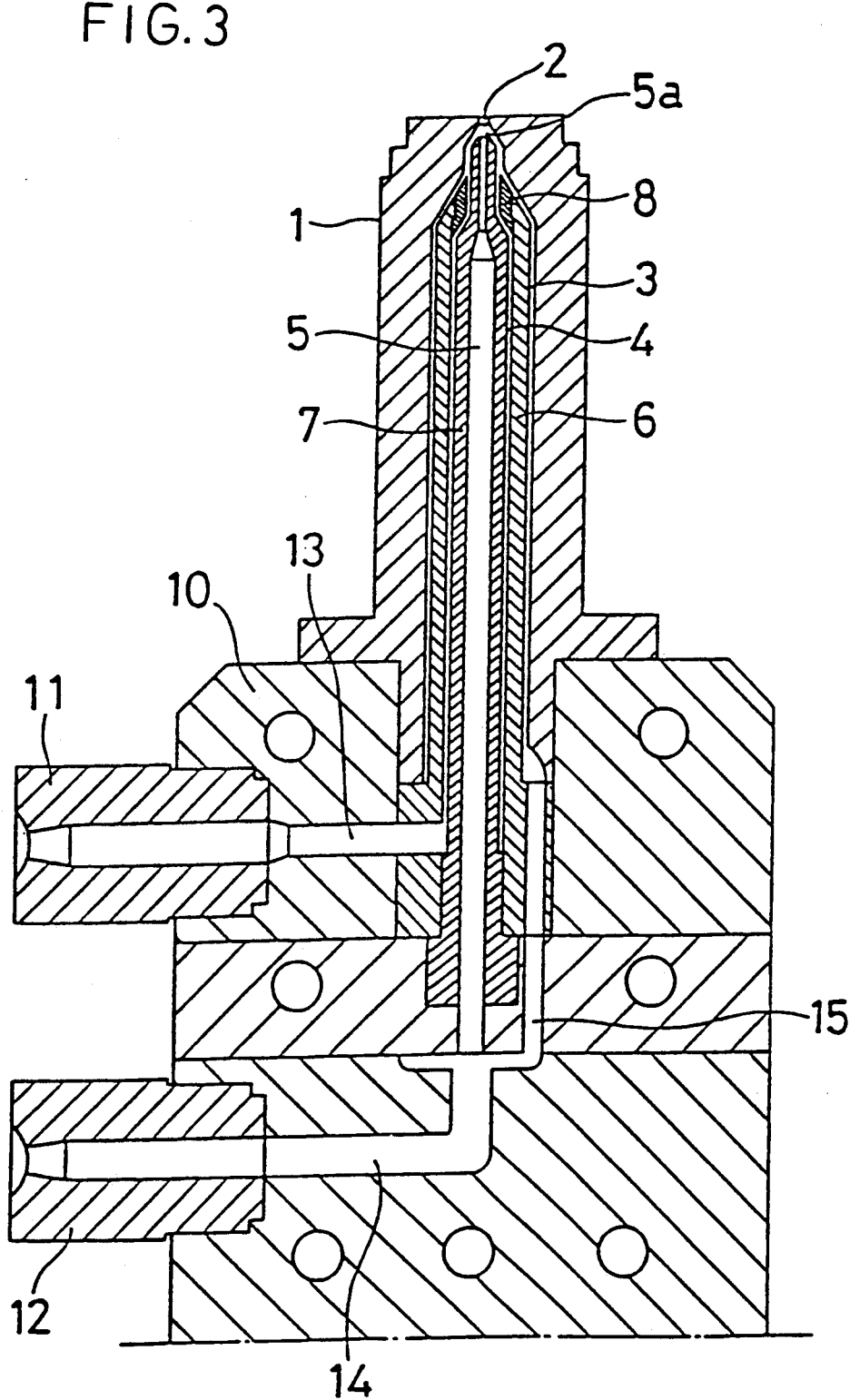
FIG. 3 is a sectional view in which a hot runner block is mounted.

The required number of the aforesaid three-layer nozzles are used while being mounted on a hot runner block 10 (FIG. 3). This embodiment shows the case where a 2-kind of resin and 3-layer molded product is molded, in which the hot runner block 10 is interiorly provided with hot runners 13 and 14 connected to sprue bushes 11 and 12, respectively, arranged on the side thereof, and the hot runner 13, the hot runner 14 and a branch path 15 of the hot runner 14 are connected to the second resin path 4, the third resin path 5 and the first resin path 3, respectively, so that the same type of resin is injected from the first and third resin paths 3 and 5, and a different type of resin is injected from the second resin path 4.

The manner in which a three-layer product having an intermediate layer is molded using the three-layer nozzle shown in FIG. 1 will now be described.

First, when injection pressure is applied to the first and third resin paths 3 and 5 to inject resin A therethrough, the valve member 8 is moved upwardly as viewed in FIG. 4 due to a pressure difference between the second resin path 4 and the third resin path 5 to close the second resin path 4 as shown in FIG. 5.

Thereby, only the same molten resin A is injected into the cavity 16. The different molten resin B of the second resin path 4 is not injected.

Subsequently, at the time of completion of the injection of a predetermined quantity of molten resin A into cavity 16, and when injection pressure is applied to the second resin path 4, the valve member 8 is moved downward, as shown in FIG. 4, due to a difference in a pressure receiving are in the valve member 8, to open the second resin path 4 so that the molten resin B is injected between the two paths of molten resin A coming from the first and third resin paths 3 and 5. The three resin layers are then injected into the cavity 16 from the injection opening 2.

After the aforesaid injection has been completed, a product having three layers as a whole is molded, and when injection pressure of the second resin path 4 is disconnected, the valve member 8 is again moved forward by the resin pressure of the third resin path 5, as shown in FIG. 5, due to a difference in resin pressure at that time, to close the second resin path 4.

Therefore, only the molten resin A is again injected into cavity 16, and a single layer is molded. The molten resin B injected from the second resin path 4 is to be positioned in the center between the two layers of molten resin A, and therefore, when the resin is filled and moved in the cavity 16, even if a skin layer caused by cooling should occur on the surfaces of the two layers of molten resin A in contact with the mold surface, the skin layer has a slow influence thereon and it is difficult for the molten resin B to form a skin layer halfway.

Figure 6:
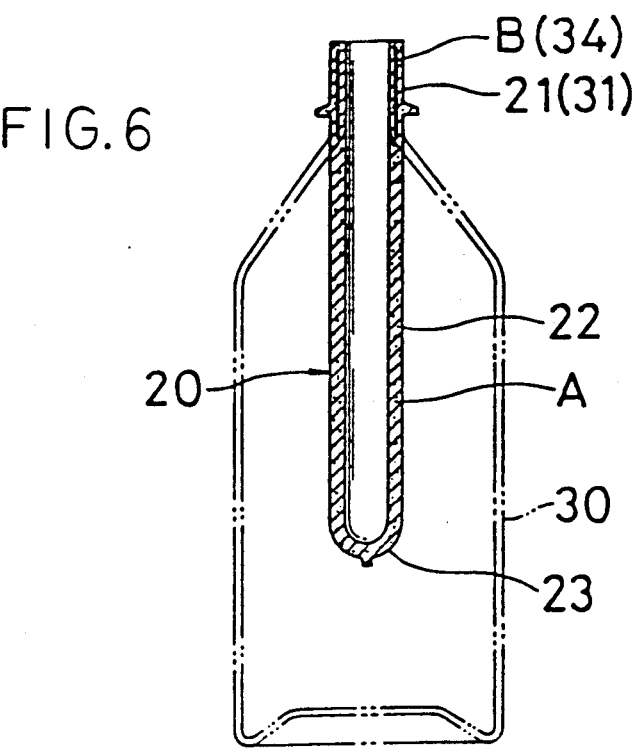
FIGS. 6 to 8 are respectively sectional view of a preform having a bottom and a container.

The molded product 20 shown in FIG. 6 is a preform having a bottom comprising a mouth portion 21 formed of three layers by injecting and filling the molten resin B of the second resin path 4 and a body 22 and a bottom 23 both formed of a single layer only formed of molten resin A, the chain line indicating a container 30 in which a preform having a bottom is orientation blow molded.

Figure 7:
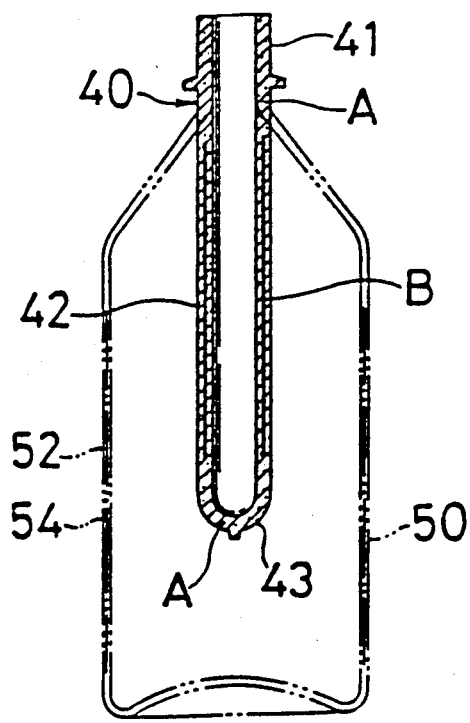

The molded product 40 shown in FIG. 7 is a preform having a three-layer body 42 (obtained by injecting the molten resin B of the second resin path 4 in between the molten resin A of the first and third resin paths 3, 5) and a mouth portion 4a and a bottom portion 43 both formed of a single layer of resin A. The chain line indicates a container 50 in which a preform having a bottom is orientation blow molded.

Figure 8:
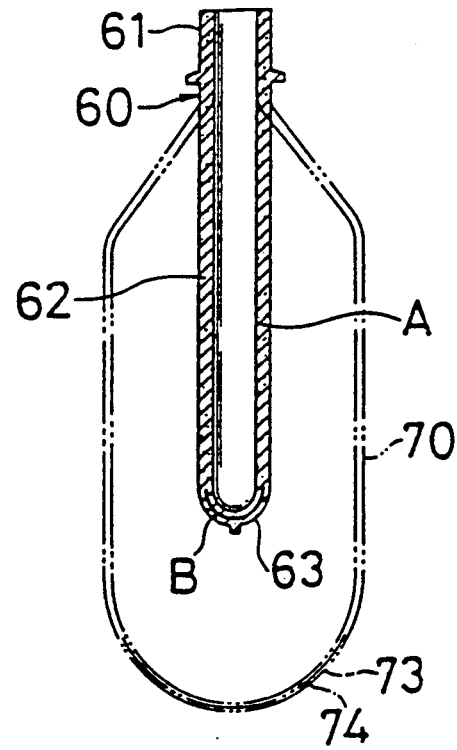

The molded product 60 shown in FIG. 8 is a preform having a three-layer bottom 73 (obtained by injecting the molten resin B of the second resin path 4 in between the molten resin A of the first and third resin paths 3, 5) and a mouth portion 61 and a body portion 62 formed of a single layer of resin A. The chain line indicates a container 70 in which a preform having a bottom is orientation blow molded.

The resin used as the molten resin A may comprise a resin such as a polyethylene terephthalate, and the molten resin B includes resins excellent in barrier properties such as methaxylene group contained polyamide, ethylene vinyl alcohol and high nitrile or resins having a heat resistance such as polycarbonate and U-polymer® (a trademark of Unichika Co., Ltd registered in Japan), which are used according to uses of containers molded thereby.

For example, when a resin forming an intermediate layer 34 comprises a polycarbonate, formation of a mouth portion 31 of a container 30 into a multi-layer remarkably improves the heat resistance as compared with the case where it merely comprises a polyethylene terephthalate to prevent the mouth portion from being changed during heating and filling.

Similarly, when a bottom 73 of a container 70 (FIG. 8) is formed into a multi-layer by an intermediate layer 74 of U-shaped polymer, the heat resistance of the bottom 73 is improved, and even if heat treatment is conducted after filling a carbonated juice, a central portion thereof is not projected and deformed as in a bottom of a single layer.

Furthermore, in a product in which only a body 52 is formed into a multi-layer by an intermediate layer formed of a methaxylene group contained polyamide, barrier properties are improved, peeling between layers when a bottom is formed into a multilayer can be prevented, and expensive resins used for the intermediate layer 54 can be saved.

Next, one example of molding conditions in the case of the three-layer nozzle shown in FIG. 1 is given below.

Sectional area of resin paths
   First resin path: 34.56 mm$^2$
   Second resin path: 59.69 mm$^2$
   Third resin path: 21.23 mm$^2$
Diameter of injection opening 2.0 to 3.0 mm
Pressure receiving area (projection area) of valve member
   Second resin path side (fore end): 25.13 mm$^2$
   Third resin path side (rear end): 21.23 mm$^2$
Resin material
   First and third resin paths
     Polyethylene terephthalate
   Second resin path
     SM nylon
Injection pressure
   First and third resin paths
     Primary pressure: 140 kg/cm$^2$
     Secondary pressure: 58 kg/cm$^2$
   Second resin path: 100 kg/cm$^2$ As mentioned above, according to this invention, a first, a second and a third resin paths are concentrically provided within a nozzle body, the second resin path being closed by a valve member which is actuated by resin pressure of the other resin paths to control a molten resin from the second resin path, whereby a position at which an intermediate layer is formed by the molten resin can be suitably set. Therefore, only the mouth portion, body or bottom of a molded product can be formed into a multilayer. Since the position of the intermediate layer can be set to a central portion, in injection molding of a multi-layer molded product, the effect is great, and it is industrially very effective and widely utilized.

We claim:

1. A multilayer nozzle, comprising:
   a first core member defining a generally cylindrical first resin path;
   a second core member encircling said first core member and cooperating with said first core member to define a generally cylindrical second resin path;
   a nozzle body encircling said second core member and cooperating with said second core member to define a generally cylindrical third resin path; said first, second and third resin paths being concentric with one another and directing resin passing through them to a common injection opening;
   a valve member cooperating with said second resin path and separate from said core members and said nozzle body and movable between a first position wherein it closes said second resin path and a second position wherein it opens said second resin path;
   responsive means associated with the valve member responsive to respective pressures of first and second resins injected into said first and second paths, respectively, to move said valve member between said first and second positions in response to changes in said respective pressures of said first and second resins in said first and second paths; and
   said first and second core members, said nozzle body and said valve member cooperating to create a multilayer resin from said first and second resins and a third resin injected under pressure into said third resin path, said multilayer resin having said second resin sandwiched between said first and third resins when said valve member is in said second position and when said first, second and third resins are injected through said first, second and third resin paths, respectively.

2. The multilayer nozzle of claim 1, wherein said valve member has respective faces facing said first and second resin paths, said faces defining said responsive means and causing said valve member to move between said first and second positions in response to said respective pressures applied to said respective faces by said first and second resins in said first and second paths.

3. The multilayer nozzle of claim 2, wherein said valve member is supported by said first core member for movement between said first and second positions.

4. The multilayer nozzle assembly of claim 3, wherein said first core member terminates at a distal end and said valve member is located on said distal end of said first core member.

5. The multilayer nozzle of claim 2, wherein said respective faces are first and second tapered surfaces each forming a respective oblique angle with a central axis of said nozzle and facing said first and second resin paths to define first and second pressure receiving areas.

6. The multilayer nozzle of claim 5, wherein the ratio between said first and second pressure receiving areas of said first and second surfaces is greater than 0.5 and less than 4.

7. The multilayer nozzle of claim 2, further comprising means for injecting said first, second and third resins under pressure into said first, second and third resins path, respectively.

8. The multilayer nozzle of claim 1, wherein said valve member is movable relative to said first core member, said second core member and said nozzle body.

9. The multilayer nozzle of claim 8, further including means for simultaneously injecting said first, second and third resins into said first, second and third resin paths, respectively, so as to cause said first and second core members, said nozzle body and said valve member to cooperate to create said multi-layer resin.

10. The multilayer nozzle of claim 1, further including means for simultaneously injecting said first, second and third resins into said first, second and third resin paths, respectively, so as to cause said first and second core members, said nozzle body and said valve member to cooperate to create said multi-layer resin.

11. The multilayer nozzle of claim 1, wherein said first and second core members and said nozzle body are stationary relative to one another.

12. A multilayer nozzle, comprising:
a first core member defining a generally cylindrical first resin path;
a second core member encircling said first core member and cooperating with said first core member to define a generally cylindrical second resin path;
a nozzle body encircling said second core member and cooperating with said second core member to define a generally cylindrical third resin path; said first, second and third resin paths being concentric with one another and directing resin passing through them to a common injection opening;
a valve member cooperating with said second resin path and movable between a first position wherein it closes said second resin path and a second position wherein it opens said second resin path;
responsive means associated with the valve member responsive to respective pressures of first and second resins injected into said second and third resin paths, respectively, to move said valve member between said first and second positions in response to changes in said respective pressures of said first and second resins in said second and third paths; and
said first and second core members, said nozzle body and said valve member cooperating to create a multilayer resin from said first and second resins and a third resin injected under pressure into said first resin path, said multilayer resin having said first resin sandwiched between said second and third resins when said valve member is in said second position and when said first, second and third resins are injected through said second, said third and said first resin paths, respectively.

13. The multilayer nozzle of claim 12, wherein said valve member has respective faces facing said second and third resin paths, said faces defining said responsive means and causing said valve member to move between said first and second positions in response to the relative pressures applied to said respective faces by said first and second resins in said second and third paths.

14. The multilayer nozzle of claim 13, wherein said valve member is supported by said second core member for movement between said first and second positions.

15. The multilayer nozzle of claim 14, wherein said second core member terminates at a distal end and said valve member is located on said distal end of said second core member.

16. The multilayer nozzle of claim 13, wherein said respective faces are first and second tapered surfaces each forming an oblique angle with a central axis of said resin paths and abutting said second and third resin paths to define first and second pressure receiving areas.

17. The multilayer nozzle of claim 16, wherein the ratio between said first and second pressure receiving areas of said first and second surfaces is greater than 0.5 and less than 4.

18. The multilayer nozzle of claim 17, further including means for injecting said first, second and third resins into said second, third and first resin paths, respectively.

19. A multilayer nozzle, comprising:
a first core member defining a generally cylindrical first resin path;
a second core member encircling said first core member and cooperating with said first core member to define a generally cylindrical second resin path;
a nozzle body encircling said second core member and cooperating with said second core member to define a generally cylindrical third resin path; said first, second and third resin paths being concentric with one another and directing resin passing through them to a common injection opening;
a valve member cooperating with said second resin path and movable relative to said first core member, said second core member and said nozzle body between a first position wherein it closes said second resin path and a second position wherein it opens said second resin path;
means associated with the valve member responsive to respective pressures of first and second resins injected into said first and second paths, respectively, to move said valve member between said first and second positions in response to changes in said respective pressures of said first and second resins in said first and second paths; and
said first and second core members, said nozzle body and said valve member cooperating to create a multilayer resin from said first and second resins and a third resin injected under pressure into said third resin path, said multilayer resin having said second resin sandwiched between said first and third resins when said valve member is in said second position and when said first, second and third resins are injected through said first, second and third resin paths, respectively.

20. A multilayer nozzle, comprising:
a first core member defining a generally cylindrical first resin path;
a second core member encircling said first core member and cooperating with said first core member to define a generally cylindrical second resin path;
a nozzle body encircling said second core member and cooperating with said second core member to define a generally cylindrical third resin path; said first, second and third resin paths being concentric with one another and directing resin passing through them to a common injection opening, said first core member, said second core member and said nozzle body being stationary relative to one another;
a valve member cooperating with said second resin path and movable between a first position wherein it closes said second resin path and a second position wherein it opens said second resin path;

means associated with said valve member responsive to respective pressures of first and second resins injected into said first and second paths, respectively, to move said valve member between said first and second positions in response to changes in said respective pressures of said first and second resins in said first and second paths; and said first and second core members, said nozzle body and said valve member cooperating to create a multilayer resin from said first and second resins and a third resin injected under pressure into said third resin path, said multilayer resin having said second resin sandwiched between said first and third resins when said valve member is in said second position and when said first, second and third resins are injected through said first, second and third resin paths, respectively.

21. A multilayer nozzle, comprising:
a first core member defining a generally cylindrical first resin path;
a second core member encircling said first core member and cooperating with said first core member to define a generally cylindrical second resin path;
a nozzle body encircling said second core member and cooperating with said second core member to define a generally cylindrical third resin path; said first, second and third resin paths being concentric with one another and directing resin passing through them to a common injection opening;
a valve member cooperating with said second resin path and movable between a first position wherein it closes said second resin path and a second position wherein it opens said second resin path;
means associated with the valve member responsive to respective pressures of first and second resins injected into said first and second paths, respectively, to move said valve member between said first and second positions in response to changes in said respective pressures of said first and second resins in said first and second paths;
means for simultaneously injecting said first resin, said second resin and a third resin into said first, second and third resin paths, respectively, the respective pressures of said first and second resins causing said valve member to move into said second position; and
said first and second core members, said nozzle body and said valve member cooperating to create a multilayer resin from said first, second and third resins, said second resin being sandwiched between said first and third resins.

* * * * *